United States Patent [19]

Ono et al.

[11] 4,362,661

[45] Dec. 7, 1982

[54] IMMUNOGLOBULIN COMPOSITION HAVING A HIGH MONOMER CONTENT, AND PROCESS FOR PRODUCTION THEREOF

[75] Inventors: Syoji Ono, Kodaira; Yuji Fukumoto, Kumamoto; Tsunemasa Yoshida, Hachioji, all of Japan

[73] Assignees: Teijin Limited, Osaka; The Chemo-Sero-Therapeutic Research Institute, Kumamoto, both of Japan

[21] Appl. No.: 175,739

[22] Filed: Aug. 6, 1980

[30] Foreign Application Priority Data

Aug. 9, 1979 [JP] Japan ............................ 54-100757
Aug. 9, 1979 [JP] Japan ............................ 54-100758

[51] Int. Cl.$^3$ ............................................ C07G 7/00
[52] U.S. Cl. ............................ 260/112 B; 424/85; 424/101
[58] Field of Search ............... 260/112 B; 424/85, 101

[56] References Cited

U.S. PATENT DOCUMENTS 4,059,571 11/1977 Tomibe et al. ............... 260/112 B
4,118,379 10/1978 Schmidtberger ............. 260/112 B

FOREIGN PATENT DOCUMENTS 2012479 2/1979 Japan .

OTHER PUBLICATIONS

Acta Chemica Scandinavica, vol. 22, 490–496 (1968), Hansson.

Primary Examiner—Howard E. Schain
Attorney, Agent, or Firm—Sherman & Shalloway

[57] ABSTRACT

An immunoglobulin composition comprising an immunoglobulin, and as an aggregation preventing agent or an aggregate dissociating agent for the immunoglobulin, about 1 to about 600% by weight, based on the weight of the immunoglobulin, of a water-soluble acid additive salt of a basic nitrogen-containing organic compound containing one or more basic nitrogen atoms in the molecule and optionally carboxyl groups in smaller number than the basic nitrogen atoms and having a pKb at 25° C. of not more than 7; and a method for producing an immunoglobulin composition having a high monomer content, which comprises contacting an immunoglobulin in aqueous solution with about 1 to about 600% by weight, based on the weight of the immunoglobulin, of a water-soluble acid addition salt thereby to prevent aggregation of the monomer of the immunoglobulin, and when the immunoglobulin contains aggregated molecules, dissociating the aggregated molecules into monomers, and thereafter, if desired, lyophilizing the resulting product.

3 Claims, No Drawings

IMMUNOGLOBULIN COMPOSITION HAVING A HIGH MONOMER CONTENT, AND PROCESS FOR PRODUCTION THEREOF

This invention relates to an immunoglobulin composition having a high monomer content, and to a process for production thereof.

Immunoglobulins are of great medical significance as agents responsible for humoral immunity, and have immune activity against various pathogenic microorganisms. Administration of immunoglobulins can therefore lead to the prevention and treatment of viral infections such as measles and viral hepatitis and of infections caused by antibiotic-resistant bacteria such as staphylococci. In such prevention and treatment, intravenous injection is preferred to intramuscular injection in order to administer large amounts of an immunoglobulin and cause it to produce a rapid effect. However, intravenous administration of an immunoglobulin fractionated from human plasma may cause anaphylactic side-effects involving hypotension, chill and pyrexia, dyspnea, headache, etc. This is because aggregated immunoglobulin molecules in the immunoglobulin fractionated from human plasma combine with complements in the blood to activate them and thereby liberate biologically active factors such as an anaphylatoxin-like substance or a vascular-permeable factor.

Such aggregarted immunoglobulins are inherently contained in the immunoglobulins fractionated from human plasma, and tend to form gradually with the passage of time during their formulation into dosage forms.

In an attempt to obtain intravenously injectable immunoglobulins free from the aforesaid defects, some methods have been suggested heretofore which include, for example, the removal of the aggregates immunoglobulin molecules, the dissociation of the aggregated molecules into monomers, or the inhibition of formation of the aggregated immunogloublin molecules.

For example, there have been proposed a method of removing the aggregated immunoglobulin molecules by subjecting an aqueous solution of an immunoglobulin to ultracentrifugation at 100,000 G, and a method of removing the aggregated immunoglobulin molecules by adding a polymeric substance such as polyethylene glycol, a salt such as ammonium sulfate, acrinol, etc. to a solution of an immunoglobulin to precipitate the aggregated immunoglobulin molecules. These methods, however, have the defect that the aggregated immunoglobulin molecules are not sufficiently removed, and moreover after the treatment, aggregation again begins. Furthermore, since these methods rely on the removal of the aggregated immunoglobulin molecules out of the system, the yield of the immunoglobulin that can be finally utilized decreases by an amount corresponding to the removed aggregated molecules.

Treatment of an immunoglobulin containing aggregated molecules with an acidic aqueous solution at a pH of 4 is known as the method for dissociating the aggregated immunogloublin molecules into monomers [see Acta Chemica Scandinavica, vol. 22, pages 490–496 (1968)]. The immunoglobulin, however, undergoes denaturation on standing for a long period of time at a pH of 4, and it is necessary to render the treating solution neutral after the treatment. At this time, the dissociated monomers again aggregate.

A method comprising treating an immunoglobulin containing aggregated molecules with plasmin, which is a protease, is also known to dissociate the aggregated immunoglobulin molecules into monomers. However, the monomers will undergo decomposition upon standing in contact with the plasmin, and it is necessary to remove the plasmin completely after the treatment. It is difficult in practice to remove the plasmin completely, and moreover, with this method, a period of several days is required to dissociate the aggregated immunoglobulin molecules.

Japanese Laid-Open Patent Publication No. 20124/79 discloses a method which comprises adding a neutral amino acid such as glycine or alanine, a sugar such as glucose or fructose, or a neutral inorganic salt such as sodium chloride or potassium chloride as a dissociating agent to gamma-globulin for intramuscular injection including aggregated molecules, thereby dissociating the aggregated gamma-globulin molecules and preventing re-formation of aggregated molecules. The specification of this Japanese Patent Publication states that in order to dissociate the aggregated gamma-globulin molecules completely into monomers, the reaction must be performed at 4° to 50° C. for 2 to 30 days, preferably at 4° C. for 20 to 30 days or at 37° C. for 3 to 7 days. Thus, because of the slow rate of reaction, this method cannot be advantageously used in commecial practice.

It is an object of this invention to provide an immunoglobulin composition having a high monomer content.

Another object of this invention is to provide an immunoglobulin composition which is substantially free from aggregated immunogloublin molecules and is suitable for intravenous injection.

Still another object of this invention is to provide an immunogloublin composition having excellent storage stability which on long-term storage, does not substantially form aggregated immunogloublin molecules.

Yet another object of this invention is to provide a method for producing an immunoglobulin composition having a high monomer content which comprises dissociating aggregated immunoglobulin molecules of preventing aggregation of immunoglobulin molecules.

Other objects and advantages of this invention will become apparent from the following description.

According to one aspect of this invention, these objects and advantages of this invention are achieved by an immunoglobulin composition comprising an immunoglobulin and as an aggregation preventing agent or an aggregate dissociating agent for the immunoglobulin, about 1 to about 600% by weight, based on the weight of the immunoglobulin, of a water-soluble acid addition salt of a basic nitrogen-containing organic compound containing one or more basic nitrogen atoms in the molecule and optionally carboxyl groups smaller in number than the basic nitrogen atoms and having a pKb at 25° C. of not more than 7.

According to another aspect, these objects and advantages of this invention are achieved by a method for producing an immunoglobulin composition having a high monomer content, which comprises contacting an immunoglobulin in aqueous solution with about 1 to about 600% by weight, based on the weight of the immunoglobulin, of a water-soluble acid addition salt of a basic nitrogen-containing organic compound containing one or more basic nitrogen atoms in the molecule and optionally carboxyl groups smaller in number than the basic nitrogen atoms and having a pKb at 25° C. of not more than 7 thereby to prevent aggregation of the monomer of the immunoglobulin, and when the immunoglobulin contains aggregated immunoglobulin molecules, dissociating them into monomers, and if desired, lyophilizing the resulting product.

The immunoglobulin used in this invention consists mainly of gamma-globulin obtained from the serum, plasma and other body fluids or extracts of organs by a known method such as the ethanol fractionating method of Cohn et al. [E. G. Cohn et al., J. Am. Chem. Soc., 68, 459 (1946)]. The immunoglobulin may be used as fractionated without purification (such an immunoglobulin usually contains at least 20% by weight of aggregated immunoglobulin molecules having a sedimentation constant of at least 9S). Or after fractionation, the immunoglobulin may be purified by purifying methods known in the art, such as treatment at pH 4, salting out, treatment with acrinol, or ion-exchange chromatography to reduce the content of aggregated immunoglobulin molecules to varying degrees, and sometimes to substantially zero.

The basic nitrogen-containing organic compound used in this invention contains one or more basic nitrogen atoms in the molecule and has a pKb at 25° C. of not more than 7. It may contain carboxyl groups which are smaller in number than the basic nitrogen atoms so long as the compound shows basicity.

As is well known, pKb used herein is a dissociation index of a basic compound which is defined by the following formula $$pKb = -\log K$$

wherein $K = [BH^+]/[B] \cdot [H^+]$ in which [b] is the concentration of the basic compound (i.e. the basic nitrogen-containing organic compound), $[H^+]$ is the hydrogen ion concentration, and $[BH^+]$ is the concentration of a conjugated acid.

Examples of suitable basic nitrogen-containing organic compounds which can be used in this invention include lower alkylamines, 5- or 6-membered heterocyclic compounds having 1 to 3 nitrogen atoms, guanidines optionally substituted by lower alkyl groups, lower alkyl- or aryl-amidines, basic amino acids, esters or amides of neutral amino acids at the carboxyl group, and amine derivatives of glucose. These basic nitrogen-containing organic compounds can be used either singly or in combination with each other.

Specific examples of the lower alkylamines are primary lower alkylamines such as methylamine, ethylamine, propylamine and butylamine, secondary lower alkylamines such as dimethylamine, diethylamine, dipropylamine and dibutylamine and tertiary lower alkylamines such as trimethylamine, triethylamine, tripropylamine and tributylamine. Preferably, the lower alkyl group in the lower alkylamines has 1 to 4 carbon atoms.

Specific examples of the 5- or 6-membered heterocyclic compounds having 1 to 3 nitrogen atoms include pyrrolidine, piperidine, imidazole, pyrazole and triazole. These compounds may be substituted with an alkyl group having 1 to 4 carbon atoms (such as 2-methylimidazole).

Specific examples of the optionally substituted guanidines are guanidine and methylguanidine. Preferably, the substituent alkyl group has 1 to 4 carbon atoms.

Specific examples of the amidines are $C_1-C_4$ alkyl amidines such as methylamidine, and benzamidines optionally substituted with a $C_1-C_4$ alkyl group, such as methylbenzamidine.

Examples of the basic amino acids are lysine, ornithine, arginine, hydroxylysine and histidine.

Specific examples of the esters or amides of neutral amino acids include esters formed between neutral amino acids such as glycine, alanine, valine, leucine, isoleucine, cysteine, cystine and methionine and alcohols, for example aliphatic alcohols having 1 to 4 carbon atoms such as methanol, ethanol, n-propanol and n-butanol, and amides formed between these neutral amino acids and primary or secondary amines having a $C_1-C_4$ alkyl group or ammonia, such as glycinamide, alaninamide and leucinamide.

The amine derivatives of glucose are, for example, compounds resulting from substitution of an amino group for at least one of the hydroxyl groups of glucose, such as D-glucosamine.

The basic nitrogen-containing organic compound is used in the form of a water-soluble acid addition salt in this invention. The water-soluble acid addition salt can be favorably prepared by using a mineral acid such as hydrochloric acid, hydrobromic acid, phosphoric acid or sulfuric acid or an organic carboxylic acid such as acetic acid. The mineral acid salts are preferred. Especially preferred are the mineral acid salts, above all hydrochlorides, of arginine, guanidin, leucinamide, imidazole, 2-methylimidazole and D-glucosamine.

The immunoglobuline composition of this invention contains about 1 to about 600% by weight, preferably 10 to 600% by weight, more preferably 20 to 400% by weight, based on the immunoglobulin, of the water-soluble acid addition salt of the basic nitrogen-containing organic compound. If the amount of the water-soluble acid addition salt is less than about 1% by weight, the effect of this compound to dissociate the aggregated immunolobulins and prevent re-aggregation of the molecular chains of the immunoglobulin becomes so small as to deviate from the range intended by the present invention. If, on the other hand, it exceeds about 600% by weight, the intended effect can be obtained by economic or operational disadvantages are caused.

The immunoglobulin composition of this invention contains the water-soluble acid addition salt of the basic nitrogen-containing organic compound as an aggregation preventing agent or as an aggregate dissociating agent for the immunoglobulin. The water-soluble acid addition salt serves to dissociate the aggregated immunoglobulin molecules and prevent aggregation of the molecules of the immunoglobulin.

The essence of this invention lies in the provision of an immunoglobulin composition which has a low content of the aggregated immunoglobulin molecules and therefore a high monomer content.

Since the immunoglobulin composition provided by this invention contains a lesser amount of aggregated immunoglobulin molecules and a much lower anticomplement activity than immunoglobulins fractionated from human plasma, it can sometimes be used directly as an immunoglobulin preparation for intravenous injection. For example, a composition in accordance with this invention comprising an immunoglobulin and 10 to 100% by weight of L-arginine hydrochloride can be directly formed into an immunoglobulin preparation for intravenous injection in a known manner.

The water-soluble acid addition salt of the basic nitrogen-containing organic compound of this invention acts not only as an aggregate dissociating agent for immunoglobulins but also as an aggregation inhibiting agent for immunoglobulins. Accordingly, the immunoglobulin composition of this invention may also be used as an intermediate in a process for producing an intravenously injectable immunoglobulin preparation from an immunoglobulin as fractionated (usually, a period of several days is required to formulate the fractionated immunoglobulin industrially into a lyophilized preparation). Specifically, the immunoglobulin preparation for intravenous injection is prepared by adding the water-soluble acid-addition salt of the basic nitrogen-containing compound to an aqueous solution of the fractionated immunoglobulin in the early stage of the process for production of the intravenously injectable immunoglobulin preparation, performing the process while inhibiting aggregation of the immunoglobulin molecules, and removing the water-soluble acid addition salt of the basic nitrogen-containing organic compound by dialysis, etc. in a step as close as possible to the final step of lyophilization, and rapidly lyophilizing the resulting aqueous solution of immunogloublin having a high monomer content.

The composition of this invention is produced by contacting an immunoglobulin containing aggregated immunoglobulin molecules with the water-soluble acid addition salt, or contacting a purified immunoglobulin substantially free from aggregated immunoglobulin molecules with the water-soluble acid addition salt.

When the immunoglobulin is contacted in aqueous solution with the water-soluble acid addition salt, dissociation of the aggregated immunoglobulin molecules proceeds, and the dissociated immunoglobulin molecules are prevented from re-aggregation.

Thus, according to this invention, there is provided a method for producing an immunoglobulin composition having a high monomer content, which comprises contacting immunoglobulines containing aggregated immunoglobulin molecules in aqueous solution with about 1 to about 600% by weight, based on the weight of the immunoglobulin, of at least one water-soluble acid addition salt of a basic nitrogen-containing organic compound containing one or more basic nitrogen atoms in the molecule and optionally carboxyl groups in smaller number than the basic nitrogen atoms and having a pKb at 25° C. of not more than 7, thereby dissociating the aggregated immunoglobulin molecules into monomers, and then if desired, lyophilizing the resulting product.

According to this invention, there is also provided a method for producing an immunoglobulin composition having a high monomer content, which comprises contacting a purified immunoglobulin substantially free from aggregated molecules in aqueous solution with about 1 to about 600% by weight, based on the weight of the immunoglobulin, of at least one water-soluble acid addition salt of a basic nitrogen-containing organic compound containing one or more basic nitrogen atoms in the molecule and optionally carboxyl groups in smaller number than the basic nitrogen atoms and having a pKb at 25° C. of not more than 7, thereby preventing aggregation of the monomer of the immunoglobulin, and then, if desired, lyophilizing the resulting product.

In the method of this invention, the immunoglobulin and the water-soluble acid addition salt of the basic nitrogen-containing organic compound are contacted in aqueous solution. The contacting is carried out at about 0° to about 50° C., preferably at about 0° to about 30° C. Desirably, the pH of the aqueous solution at the time of contact is about 5 to about 8.

The greatest characteristic of the method of this invention is that as soon as the aggregated immunoglobulin molecules in the starting immunoglobulin are contacted with the water-soluble acid addition salt under the aforesaid contacting conditions, dissociation of the aggregated molecules begins, and within a period of as short as 1 hour, dissociation of the aggregated immunoglobulin molecules can be substantially achieved and thereby an immunoglobulin having a high monomer content can be provided.

A second feature of this invention is that even when the contacting is continued for a period beyond the aforesaid time, substantial dissociation of the aggregated immunoglobulin molecules is retained over a long period of time.

In the latter-mentioned method, the water-soluble acid addition salt may also be produced in situ by preparing an aqueous solution of the basic nitrogen-containing organic compound and adding to the aqueous solution an acid such as hydrochloric acid capable of converting the basic nitrogen containing organic compound into the water-soluble acid addition salt, to adjust its pH to about 5 to 8.

According to the method of this invention, the resulting aqueous solution of immunoglobulin having a high monomer content, if required, can be lyophilized by a method known per se to provide the composition of this invention in the form of a lyophilized solid. Preferably, the composition of this invention provided in the form of a lyophilized solid is an intravenously injectable composition comprising a non-toxic water-soluble acid addition salt capable of being used in intravenous injection. Such an intravenously injectable composition is dissolved in sterilized water or physiological saline to form an intravenous injecting preparation.

Preferably, the composition of this invention provided in the form of a lyophilized solid contains about 1 to about 100% by weight, based on the weight of the immunoglobulin, of a nontoxic water-soluble acid addition salt such as L-arginine hydrochloride.

As can be appreciated from the foregoing, the method of this invention includes the following embodiments so long as the aggregated immunoglobulin molecules can be substantially dissociated and aggregation of the immunoglobulin molecules is substantially inhibited.

(1) A method comprising contacting an immunoglobulin containing about at least about 20% by weight of aggregated molecules and prepared by the Cohn's ethanol fractionating method with the water-soluble acid addition salt in aqueous solution. If the immunoglobulin is provided as a lyophilized product, it is used as an aqueous solution. A solid mixture of such a solid immunoglobulin and a predetermined amount of the water-soluble acid addition salt should be understood as constituting part of the immunoglobulin composition of this invention because by converting it into an aqueous solution, substantial dissociation of the aggregated immunoglobulin molecules can be achieved.

(2) A method comprising contacting an immunoglobulin treated with an acid by the method of Hanson et al. [Acta Chemica Scandinavica, vol. 22, pages 490–496 (1968)] with the water-soluble acid addition salt in aqueous solution. When the immunoglobulin treated with an acid by the method of Hanson et al, is adjusted to a pH near neutrality, the immunoglobulin molecules again aggregate. Moreover, when the immunoglobulin is maintained at a pH of about 4 for a long period of time, it undergoes denaturation. Thus, it is desirable to perform the acid treatment as immediately as possible before contact with the water-soluble acid addition salt.

(3) A method comprising contacting a purified immunoglobulin substantially free from aggregated molecules with the water-soluble acid addition salt in aqueous solution. This method is naturally performed when the contacting time elapses in the methods (1) and (2).

The present invention provides the following types of composition.

(1) An immunoglobulin composition being substantially free from aggregated molecules and being in the form of an aqueous solution capable of being directly used for intravenous injection.

(2) An immunoglobulin composition in the form of a lyophilized solid which does not substantially contain aggregated molecules and can be used as an intravenous injecting preparation by being formed into an aqueous solution.

(3) An immunoglobulin composition which does not substantially contain aggregated molecules but is in the form of an aqueous solution which cannot be directly used as an intravenous injecting preparation. An intravenously injectable immunoglobulin preparation can be prepared by removing the water-soluble acid addition salt from this composition not suitable for intravenous injection.

(4) An immunoglobulin composition in the form of a lyophilized solid which does not substantially contain aggregated molecules but cannot be used for intravenous injection even when it is formed into an aqueous solution. An intravenously injectable immunoglobulin preparation can be prepared from this type of composition by first dissolving it in water to form an aqueous solution, and then treating the aqueous solution in the same way as in the case of the composition (3) described above.

The following Examples and Comparative Examples illustrate the present invention in detail. All percentages in these examples are by weight.

In these examples, the monomer content and the anticomplement activity of an immunoglobulin were measured by the following methods.

Monomer content of immunoglobulin

The content of monomers (sedimentation constant 7S; molecular weight about 160,000) is determined by subjecting 0.3 ml of a 5% aqueous solution of an immunoglobulin. Sepharose CL-6B (Pharmacia Co.) is used as a gel, and a column having a diameter of 1.5 cm and a length of 30 cm is used. The rate of flow of the solution is 1/6 ml/min.

Anticomplement activity

A 1% immunoglobulin solution containing guinea pig serum, 20 $CH_{50}$/ml, adjusted to 5 ml with $GVB^{++}$ is incubated at 37° C. for an hour, and the consumed complement is measured by the method described in Kabat & Mayer, "Experimental Immunochemistry," page 225, 1961. The anticomplement activity levels are indicated by the percentage of consumption to 20 $CH_{50}$/ml.

EXAMPLES 1 TO 12 AND COMPARATIVE EXAMPLES 1 TO 4

A predetermined amount of each of the additives shown in Table 1 (the water-soluble acid addition salts of basic nitrogen-containing organic compounds having a pKb of not more than 7 in accordance with this invention or comparative additives) was added to 10 ml of a 5% solution of human immunoglobulin (fraction II obtained by the Cohn's ethanol fractionating method; a product of Armour Co.) (monomer content 76.3%; anticomplement acitivity more than 90). One hour later, the content of monomer and the anticomplement value of the immunoglobulin were measured. The results are shown in Table 1.

TABLE 1

| Example (Ex.) or Comparative Example (CEx.) | Additive Type | $pKb^{25}$ | Amount (g) | Monomer content (%) | Anti-complement activity |
|---|---|---|---|---|---|
| Ex. 1 | L-arginine hydrochloride | 1.52 | 0.25 | 88.6 | 29.8 |
| Ex. 2 | L-arginine hydrochloride | 1.52 | 0.5 | 90.7 | 20.0 |
| Ex. 3 | L-arginine hydrochloride | 1.52 | 1 | 90.5 | 18.8 |
| Ex. 4 | L-lysine hydrochloride | 3.47 | 1 | 85.0 | 33.0 |
| Ex. 5 | L-leucinamide hydrochloride | 4.40 | 1 | 89.7 | 22.8 |
| Ex. 6 | Guanidine hydrochloride | 0.6 | 1 | 91.4 | 14.5 |
| Ex. 7 | Benzamidine hydrochloride | — | 1 | 88.4 | 29.5 |
| Ex. 8 | Triethylamine hydrochloride | 3.28 | 1 | 86.6 | 35.5 |
| Ex. 9 | Ethylamine hydrochloride | 3.37 | 1 | 86.6 | 31.8 |
| Ex. 10 | D-glucosamine hydrochloride | — | 0.5 | 87.2 | 26.4 |
| Ex. 11 | Imidazole hydrochloride | 6.97 | 1 | 88.2 | 20.0 |
| Ex. 12 | 2-Methylimidazole hydrochloride | 6.55 | 1 | 87.5 | 15.3 |
| CEx. 1 | None | — | 0 | 76.3 | 90< |
| CEx. 2 | Glycine | — | 1 | 78.4 | 90< |
| CEx. 3 | Glucose | — | 2 | 76.3 | 90< |
| CEx. 4 | Sodium chloride | — | 1 | 79.8 | 25.9 |

As can be appreciated from the detailed description above, the method of this invention makes it possible to dissociate the aggregated molecules of an immunoglobulin, and to prevent aggregation of the immunoglobulin molecules. Accordingly, the invention also brings about the excellent advantage that aggregated molecules can be utilized as dissociated immunoglobulins which can be intravenously injected.

It is seen from Table 1 that immunoglobulins obtained by adding the water-soluble acid addition salts of basic nitrogen-containing organic compounds having a dissociation index pKb of not more than 7 (Examples 1 to 12) have a higher monomer content and a much lower anticomplement activity than those obtained in Comparative Examples 1 to 4 because the aggregated molecules of the immunoglobulin are dissociated.

EXAMPLES 13 TO 23 AND COMPARATIVE EXAMPLES 5 TO 8

10 ml of a 10% solution of human immunoglobulin (fraction II obtained by the Cohn's ethanol fractionating method) was dialyzed with a 0.1 M acetate buffer having a pH of 4, and then treated with an acid by the method of Hanson et al. [see Acta Chemica Scandinavica, vol. 22, pages 490–496, 1968]. Then, it was neutralized by dialyzing it against a 0.05 M phosphate buffer (pH=7.0) containing 0.50 M of sodium chloride to obtain 12 ml of acid-treated gamma-globulin having a pH of 4 (concentration 8%).

A predetermined amount of each of the additives (the water-soluble acid addition salts of the basic nitrogen containing organic compounds having a dissociation index pKb of not more than 7 and comparative additives) shown in Table 2 was added to 10 ml of a 5% solution of the acid-treated gamma-globulin. The monomer content and the anticomplement activity of the acid-treated gamma-globulin were measured on hour after the addition and after standing for a week at 4° C. The results are shown in Table 2.

EXAMPLE 25

A 10% solution of human immunoglobulin (fraction II obtained by the Cohn's ethanol fractionating method) was treated with acrinol to remove aggregated molecules. To 10 ml of a 5% solution of the purified human immunoglobulin was added 1 g of L-arginine hydrochloride. The mixture was allowed to stand at 4° C. for 1 week. The product had an atincomplement activity of 19.6 and a monomer content of 91.5%. When L-arginine hydrochloride was not added, the human immunoglobulin had an anticomplement activity of 57.0, and a monomer content of 77.2%.

EXAMPLE 26

Powder of human immunoglobulin (fraction II obtained by the Cohn's ethanol fractionating method) was dissolved to a concentration of 2% in water containing 0.2% of human albumin and 2% of polyethylene glycol (PEG 4000). The pH of the aqueous solution was adjusted to 5.1, and the resulting turbidity (aggregated molecules) was removed by centrifugation. The polyethylene glycol concentration of the supernatant liquid

TABLE 2

| Example (Ex.) or Comparative Example (CEx.) | Additive Type | Amount (g) | One hour after addition Monomer content (%) | One hour after addition Anti-complement activity | One week after addition Monomer content (%) | One week after addition Anti-complement activity |
|---|---|---|---|---|---|---|
| Ex. 13 | L-arginine hydrochloride | 0.1 | 89.4 | 30.5 | 88.2 | 36.7 |
| Ex. 14 | L-arginine hydrochloride | 0.25 | 90.1 | 25.7 | 89.3 | 30.4 |
| Ex. 15 | L-arginine hydrochloride | 0.5 | 91.2 | 21.0 | 91.3 | 21.7 |
| Ex. 16 | L-arginine hydrochloride | 1 | 93.0 | 16.7 | 93.4 | 17.0 |
| Ex. 17 | L-lysine hydrochloride | 1 | 88.5 | 32.0 | 88.5 | 31.8 |
| Ex. 18 | L-leucinamide hydrochloride | 1 | 93.0 | 18.3 | 92.3 | 18.5 |
| Ex. 19 | Guanidine hydrochloride | 1 | 94.0 | 16.3 | 94.7 | 16.3 |
| Ex. 20 | Triethylamine hydrochloride | 1 | 88.0 | 31.3 | 87.7 | 35.5 |
| Ex. 21 | D-glucosamine hydrochloride | 0.5 | 90.7 | 27.5 | 90.2 | 28.0 |
| Ex. 22 | Imidazole hydrochloride | 0.5 | 90.0 | 20.1 | 90.3 | 19.5 |
| Ex. 23 | 2-Methylimidazole hydrochloride | 0.5 | 92.1 | 14.7 | 91.5 | 14.8 |
| CEx. 5 | None | 0 | 88.0 | 31.3 | 74.8 | 55.5 |
| CEx. 6 | Glycine | 1 | 88.4 | 31.3 | 76.5 | 55.5 |
| CEx. 7 | Glucose | 1 | 87.7 | 31.3 | 77.3 | 57.1 |
| CEx. 8 | Sodium chloride | 1 | 86.8 | 23.2 | 75.2 | 25.9 |

It is seen from Table 2 that immunoglobulin compositions (Examples 13 to 23) obtained by adding the water-soluble acid addition salts of the basic nitrogen-containing organic compounds having a dissociation index pKb of not more than 7 have a lower level of the concentration of aggregated molecules, and re-formation of aggregated molecules is inhibited over a longer period of time, than in the case of immunoglobulin compositions obtained in the Comparative Examples.

EXAMPLE 24

A 10% solution of human immunoglobulin (fraction II obtained by the Cohn's ethanol fractionating method) was purified by salting out with sodium sulfate. To 10 ml of a 5% solution of the purified human immunoglobulin was added 1 g of L-arginine hydrochloride. The mixture was allowed to stand at 4° C. for 1 week. The resulting mixture had an anticomplement activity of 21.5 and a monomer content of 93.0%. When L-arginine hydrochloride was not added, the immunoglobulin had an anticomplement activity of 57.2 and a monomer content of 76.5%.

was increased to 4% by adding a 50% solution of PEG 4000. After standing for one hour, the resulting precipitate (aggregated molecules) was removed by centrifugation. Ethanol was gradually added to the supernatant liquid at 0° C. until the concentration became 6%. The mixture was allowed to stand overnight, and the resulting precipitate (aggregated molecules) was removed by centrifugation. Then, the pH of the mixture was adjusted to 8.0, and ethanol was further added to adjust the concentration of ethanol to 25%. The resulting turbidity (composed mainly of monomer) was collected by centrifugation, and dissolved in 0.9% aqueous solution of sodium chloride, and the solution was further dialyzed against 0.9% sodium chloride. The monomer content of the dialyzed solution was 93.2%. Arginine hydrochloride was added to a concentration of 5%. On standing for a week, the monomer content was 93.5%. When arginine hydrochloride was not added, the monomer content was 85.2% on standing for a week.

EXAMPLES 27 TO 38 AND COMPARATIVE EXAMPLES 9 TO 12

A predetermined amount of each of the additives shown in Table 3 was added to 10 ml of a 5% solution of human immunoglobulin (fraction II obtained by the Cohn's ethanol fractionating method). The gamma-globulin monomer content and anticomplement activity were measured one hour after the addition and after standing at 4° C. for 3 weeks. The results are shown in Table 3.

20 contains an immunoglobulin which can be used for intravenous injection.

Immunoglobulins containing no additive (Comparative Examples 1, 5 and 9), immunoglobulins containing glycine as an additive (Comparative Examples 2, 6 and 10) and immunoglobulins containing glucose as an addi-

TABLE 3

| Example (Ex.) or Comparative Example (CEx.) | Additive | | One hour after addition | | Three weeks after addition | |
|---|---|---|---|---|---|---|
| | Type | Amount (g) | Monomer content (%) | Anti-complement activity | Monomer content (%) | Anti-complement activity |
| Ex. 27 | L-arginine hydrochloride | 0.25 | 88.6 | 29.8 | 86.4 | 30.7 |
| Ex. 28 | L-arginine hydrochloride | 0.5 | 90.7 | 20.0 | 89.2 | 20.4 |
| Ex. 29 | L-arginine hydrochloride | 1 | 90.5 | 18.8 | 90.0 | 19.0 |
| Ex. 30 | L-lysine hydrochloride | 1 | 85.0 | 33.0 | 85.6 | 36.0 |
| Ex. 31 | L-leucinamide hydrochloride | 1 | 89.7 | 22.8 | 90.5 | 24.2 |
| Ex. 32 | Guanidine hydrochloride | 1 | 91.4 | 14.5 | 90.3 | 15.0 |
| Ex. 33 | Benzamidine hydrochloride | 1 | 88.4 | 29.5 | 86.3 | 28.8 |
| Ex. 34 | Triethylamine hydrochloride | 1 | 86.6 | 35.5 | 86.4 | 34.2 |
| Ex. 35 | Ethylamine hydrochloride | 1 | 86.6 | 31.8 | 87.2 | 33.4 |
| Ex. 36 | D-glucosamine hydrochloride | 0.5 | 87.2 | 26.4 | 88.5 | 27.8 |
| Ex. 37 | Imidazole hydrochloride | 1 | 88.2 | 20.0 | 89.4 | 18.7 |
| Ex. 38 | 2-Methylimidazole hydrochloride | 1 | 87.5 | 15.3 | 88.7 | 16.4 |
| CEx. 9 | None | 0 | 76.3 | 90< | 66.5 | 90< |
| CEx. 10 | Glycine | 1 | 78.4 | 90< | 69.7 | 90< |
| CEx. 11 | Glucose | -2 | 76.3 | 90< | 65.2 | 90< |
| CEx. 12 | Sodium chloride | 1 | 79.8 | 25.9 | 70.4 | 30.5 |

It is seen from Table 3 that immunoglobulin compositions (Examples 27 to 38) obtained by adding the water-soluble acid addition salts of basic nitrogen-containing organic compounds having a dissociation index pKb of not more than 7 have a higher monomer content and a much lower anticomplement activity than those obtained in Comparative Examples because the aggregated molecules were dissociated, and that such monomer contents and anticomplement activities are substantially retained even after standing for 3 weeks.

EXAMPLES 39 AND 40

To 10 ml of a 5% solution of human immunoglobulin (fraction II obtained by the Cohn's ethanol fractionating method) was added 0.5 g of L-arginine hydrobromide or 1 g of guanidine hydrobromide. The results obtained are shown in Table 4.

TABLE 4

| | Additive | | One hour after addition | | One week after addition | |
|---|---|---|---|---|---|---|
| Example | Type | Amount (g) | Monomer content (%) | Anti-complement activity | Monomer content (%) | Anti-complement activity |
| 39 | L-arginine hydrobromide | 0.5 | 91.5 | 22.0 | 91.0 | 22.2 |
| 40 | Guanidine hydrobromide | 1.0 | 93.7 | 16.8 | 93.9 | 17.0 |

In Tables 1 to 4, the monomer content and the anticomplement activity generally seem to be correlated to each other. It is noted that as the monomer content increases, the anticomplement activity generally tends to decrease. It may be said that a composition having a low anticomplement activity of generally not more than tive (Comparative Examples 3, 7 and 11) have a high anticomplement activity and a low monomer content, and with time, their monomer contents gradually decrease. These results show that glycine and glucose cannot be substantially used as a dissociating agent for the aggregated molecules of immunoglobulins or as an aggregation inhibitor for immunoglobulins.

When sodium chloride was used (Comparative Examples 4, 8 and 12), substantially the same tendency as in the case of using glycine or glucose is noted. It is clearly seen that when sodium chloride is used, the anticomplement activity of an immunoglobulin is lower than in the case of using glycine or glucose, but the monomer content is much the same as in the case of using glycine or glucose. It is presumed therefore that a correct anticomplement activity is not shown because sodium chloride exerts some influence on the assay system for anticomplement activity.

What we claim is:

1. A method for producing a native immunoglobulin composition having a high monomer content, which comprises contacting a native immunoglobulin in aqueous solution with about 10 to about 600% by weight, based on the weight of the native immunoglobulin, of a water-soluble acid addition salt of a basic amino acid having a pKb at 25° C. of not more than 7 at a temperature between about 0° and about 50° C. in the absence of freezing and at a pH between about 5 and about 8, thereby to prevent aggregation of the monomer of the native immunoglobulin in the aqueous solution, and when the native immunoglobulin contains aggregated molecules, dissociating the aggregated molecules in the aqueous solution into monomers.

2. The process of claim 1 including the additional step of lyophilizing the immunoglobulin product.

3. The process of claim 1 or 2, wherein said basic amino acid is at least one member selected from the group consisting of lysine, ornithine and arginine.

* * * * *